(12) United States Patent
Mittal

(10) Patent No.: US 9,237,870 B2
(45) Date of Patent: Jan. 19, 2016

(54) DEVICE AND METHOD FOR PROCESSING HEART SOUNDS FOR AUSCULATION

(71) Applicant: KONINKLIJKE PHILIPS N.V., Eindhoven (NL)

(72) Inventor: Chetan Mittal, Jalandhar (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/353,296

(22) PCT Filed: Oct. 19, 2012

(86) PCT No.: PCT/IB2012/055723
§ 371 (c)(1),
(2) Date: Apr. 22, 2014

(87) PCT Pub. No.: WO2013/061221
PCT Pub. Date: May 2, 2013

(65) Prior Publication Data
US 2014/0288452 A1    Sep. 25, 2014

(30) Foreign Application Priority Data
Oct. 28, 2011   (IN) .......................... 3689/CHE/2011

(51) Int. Cl.
*A61B 5/0402*   (2006.01)
*A61B 5/00*     (2006.01)
*A61B 7/04*     (2006.01)

(52) U.S. Cl.
CPC ............. *A61B 5/7257* (2013.01); *A61B 5/0402* (2013.01); *A61B 5/7203* (2013.01); *A61B 5/7246* (2013.01); *A61B 7/04* (2013.01)

(58) Field of Classification Search
CPC .... A61B 5/726; A61B 5/7225; A61B 5/7214; A61B 5/7257; A61B 5/7203; A61B 5/7264; A61B 5/7282; A61B 7/00; A61B 5/72; A61B 5/02028; A61B 5/7246; A61B 5/7235; A61B 5/00; A61B 5/0004; A61B 5/04525; A61B 5/7221; A61B 2019/5263; A61B 5/7253; G06F 19/3418; G06F 17/148; G06F 19/3487; G06F 19/00; G06F 19/34; G06F 17/14; G06K 9/00523; G06K 9/00516; G06K 9/0053; G06K 9/0051; G06Q 50/22
See application file for complete search history.

(56) References Cited

U.S. PATENT DOCUMENTS

| 4,792,145 A | 12/1988 | Eisenberg et al. |
| 6,368,283 B1 | 4/2002 | Xu et al. |
| 7,819,814 B2 * | 10/2010 | Gavriely et al. ............... 600/528 |
| 2004/0228494 A1 | 11/2004 | Smith |
| 2008/0273709 A1 | 11/2008 | Thiagarajan et al. |
| 2008/0287819 A1 | 11/2008 | Gregson et al. |
| 2009/0043216 A1 | 2/2009 | Lin et al. |
| 2010/0027802 A1 | 2/2010 | Ravindran |

FOREIGN PATENT DOCUMENTS

WO    2009009761 A1    1/2009

* cited by examiner

*Primary Examiner* — Deborah Malamud

(57) ABSTRACT

A device for independently and controllably amplifying components of the heart sound signals without removing any component of the signal by filtering. With such a device all the signal components that carry information are still available and can be useful to a user. Filtering may however be applied to very high frequency signals, compared to the signal of interest, that are totally unrelated to the heart sounds.

12 Claims, 4 Drawing Sheets

DEVICE AND METHOD FOR PROCESSING HEART SOUNDS FOR AUSCULATION

FIELD OF THE INVENTION

The following belongs to the field of aids for auscultation.

BACKGROUND OF THE INVENTION

Auscultation forms an important part of clinical examination for screening patients with or suspected to have heart disease. Automatic identification of patterns in heart sounds is useful for assisted diagnosis. The beat to beat duration of the heart cycle varies in every individual and so do the cyclic content, for example, systolic duration and corresponding murmur. Heart sounds are often superimposed by noises including ambient noise and breathing noise, for example. For a more effective auscultation or for automatic analysis of heart sounds, it is important to identify the aperiodic noise and the periodic signals for better diagnosis. The breathing noise itself may be useful in reaching more accurate diagnosis and the presence of adequate amount of ambient noise may enhance signal perception by physicians.

The electronic processing of heart sound signals depends on some form of filtering to reduce the energy of noise in the overall signal. Even though the heart sound signals lie essentially below 200 Hz, for instance, some components lie above this frequency as well. Thus, using a low pass filter to improve the signal to noise ratio (SNR) of the heart sounds may not be the ideal way.

The document US 20080273709-A1 describes a device that processes heart sound signals, wherein an analysis tool includes an interaction tuner, a processing tuner and an output tuner. The interaction tuner includes a preset tuning selector and a dynamic range tuning selector. The processing tuner includes a band pass filter and an algorithmic extraction engine which applies extraction algorithms to the electric heart signals, segments them and extracts signals of interest.

SUMMARY OF THE INVENTION

It is desirable to have a device for and a method of independently and controllably amplifying or attenuating components of the heart sound signals without removing any component of the signal by filtering. With such a device all the signal components that carry information are still available and can be useful to a user. Filtering may however be applied to very high frequency signals, compared to the signal of interest, that are totally unrelated to the heart sounds.

Such a device for processing a signal representative of heart sounds comprises a segmenter for segmenting a signal representative of heart sounds into individual heart sound cycles, a selector for selecting a cycle as a template, the selecting based on the signal to noise ratio of the cycle, a difference generator for subtracting the template from a cycle for obtaining an extracted component, an amplifier with amplification means with independent amplification control means for controlling their gains independently, for amplifying a concatenated inverse Fourier transform of the extracted signals and the inverse Fourier transform of the template and a combiner for combining the amplified signals for outputting a combined signal.

Such a device separates two components of the signal. The two components may then be independently amplified or attenuated and replayed in synchronism. Depending on the need, any one of the components may be completely eliminated and the other amplified to the required level for further use. The signal thus processed may be used by a clinician for diagnoses or be routed to an automated device for automatic diagnosis.

It must be noted here that the device described above may be configured to process signals in real time or those stored in a memory or both, depending on the application or the need. It must also be noted that the term amplification could also mean attenuation since when a signal is being attenuated it may be deemed to be amplified with an amplification factor less than unity.

A method of processing a heart sound signal of a subject is also disclosed herein. The method comprises the steps of a segmenting step of segmenting a single cycle of a heart beat signal, a Fourier transform step of carrying out a Fourier transform of the cycle, a signal to noise ratio determination step of determining the signal to noise ratio of the cycle, a selection step of selecting the signal with the largest signal to noise ratio as a template, a subtraction step of subtracting the template from a single cycle signal to obtain a noise component of the cycle, a restoration step of obtaining the inverse Fourier transform of the individual cycles and the template, an amplification step of controllably amplifying each component individually and a summation step of adding the components for outputting a combined signal.

The different embodiments of the device and variants of the method are described in detail hereinafter with reference to the following drawings wherein:

BRIEF DESCRIPTION OF THE DRAWINGS

The different embodiments of the device and variants of the method are described in detail hereinafter with reference to the following drawings wherein.

DETAILED DESCRIPTION OF EMBODIMENTS

Figure 1:
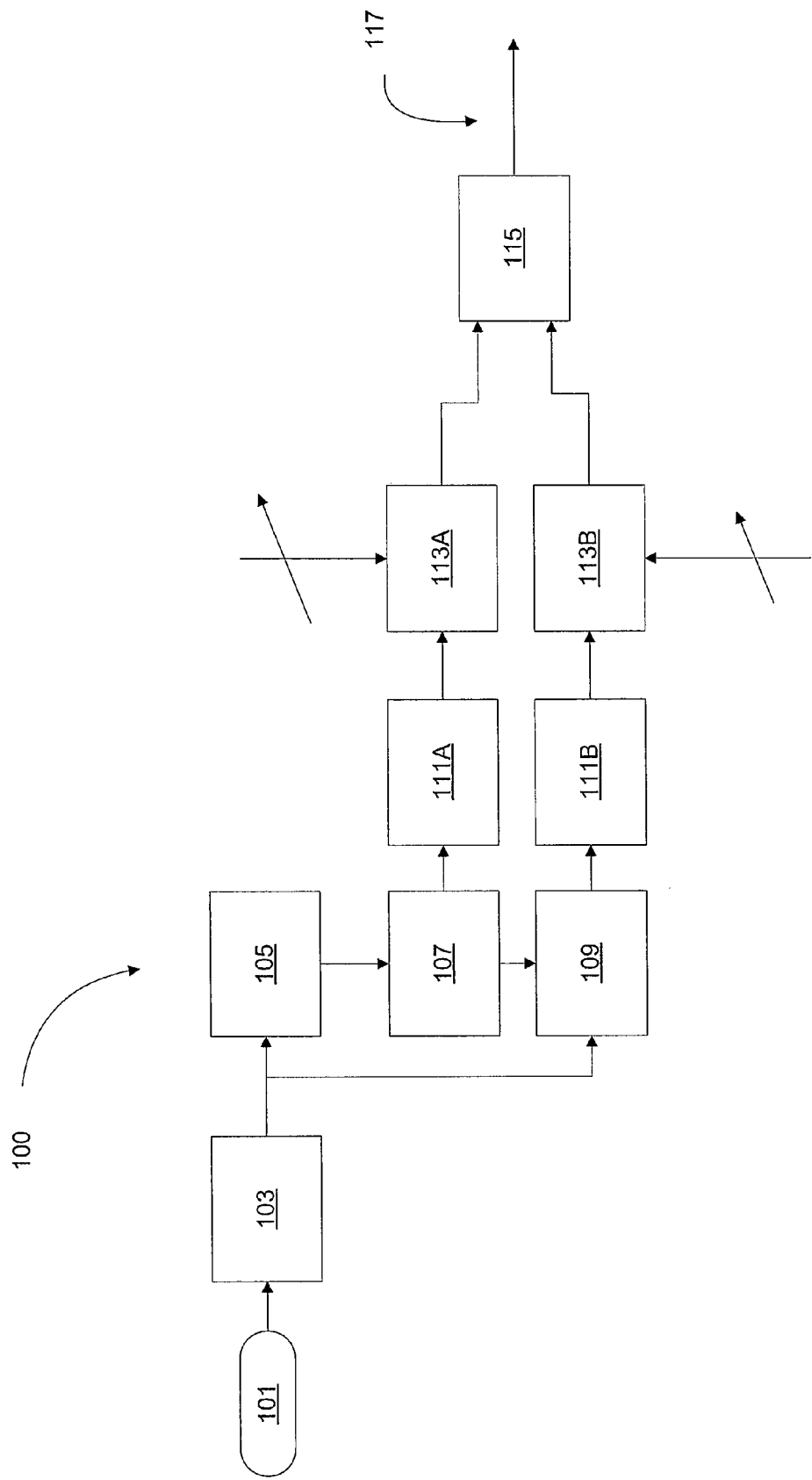
FIG. 1 is a schematic block diagram of an embodiment of the disclosed device
Figure 2:
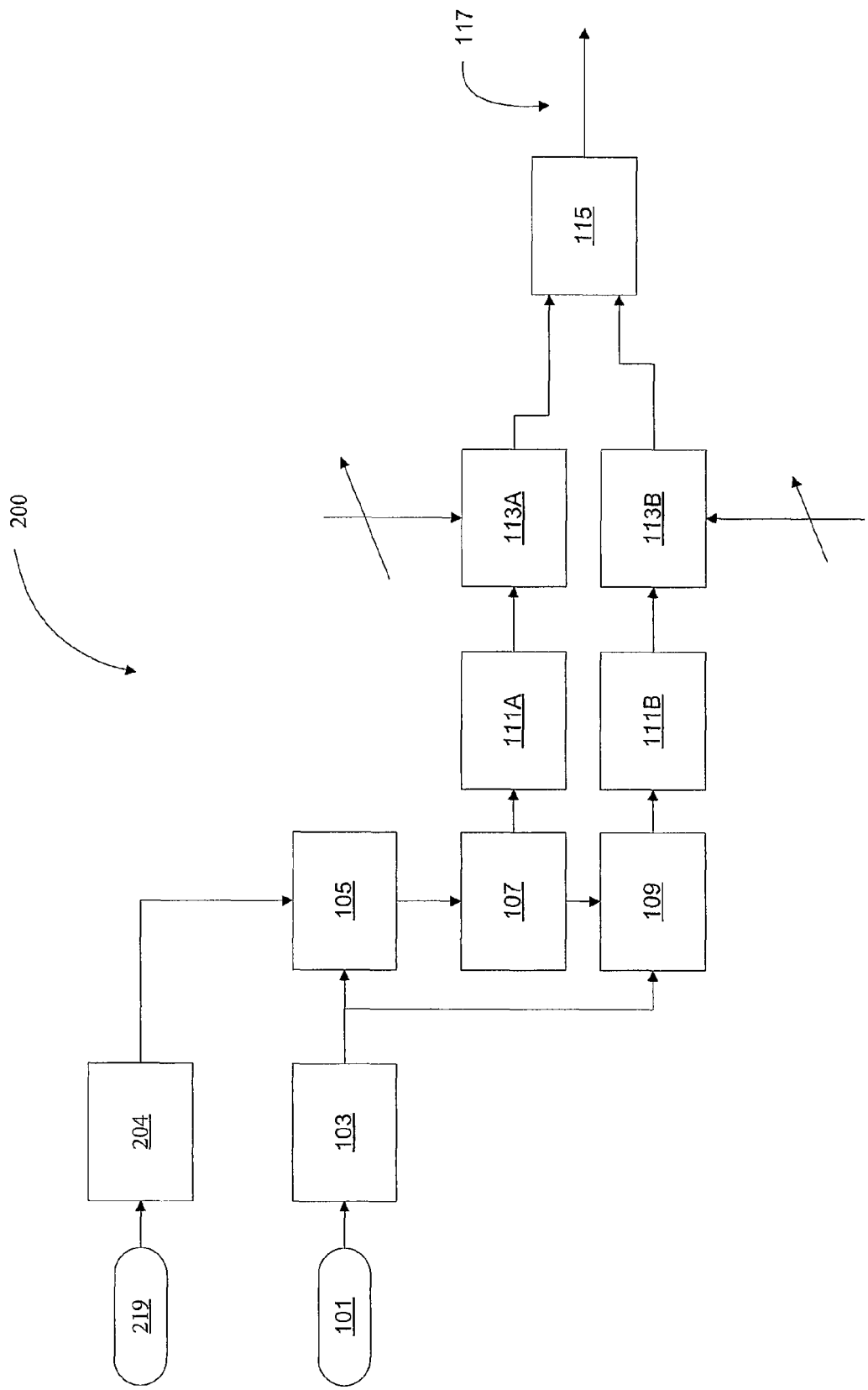
FIG. 2 is a schematic block diagram of an embodiment of the disclosed device wherein additionally an ecg signal may be acquired.
Figure 3:
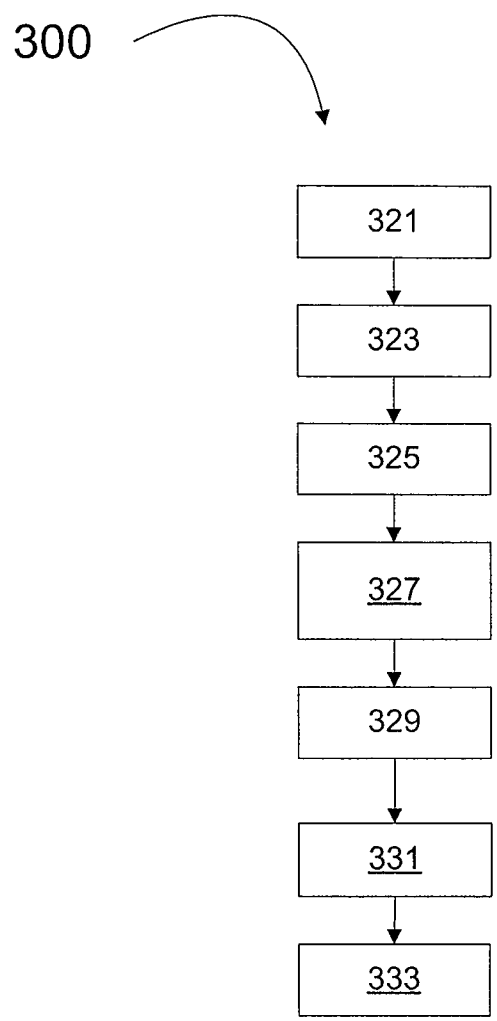
FIG. 3 is a schematic representation of the method of the an embodiment of the disclosed device.
Figure 4:
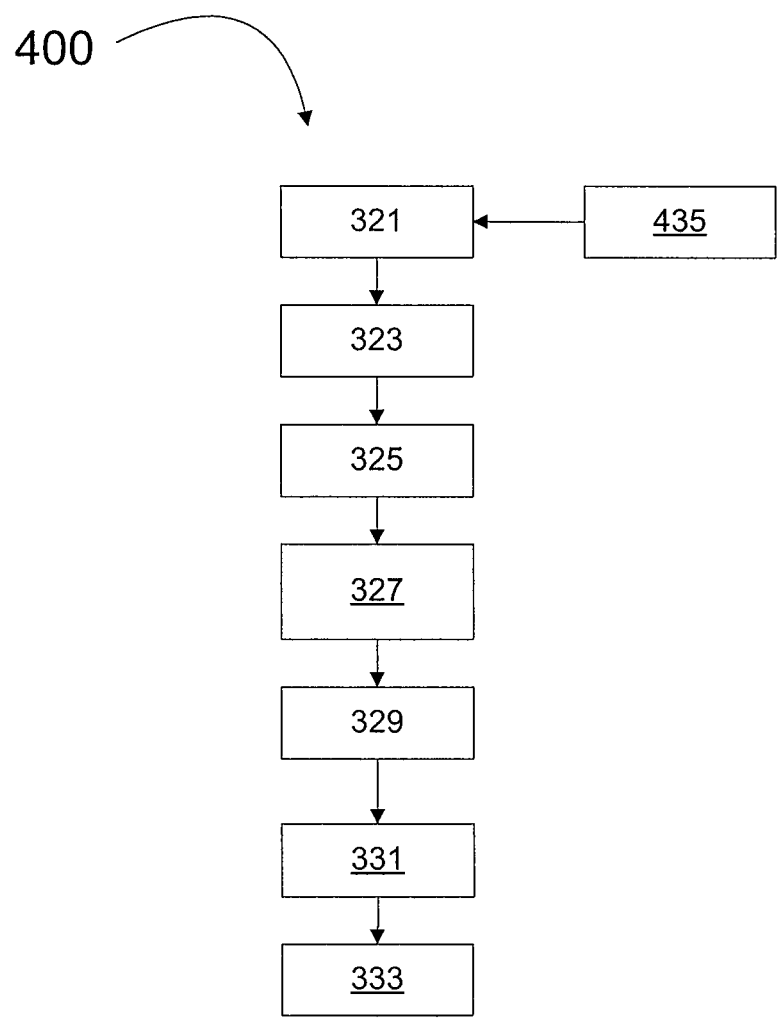
FIG 4. is schematic representation of a method of an embodiment of the disclosed device wherein segmentation of heart cycles are assisted by ecg signals.

FIG. 1 shows a schematic block diagram of an embodiment of the disclosed device. The heart sound sensor 101 senses the heart sounds from the surface of the thorax of a subject. An Analog to Digital Converter (ADC) 103 converts the signal into a digital signal. The heart sounds are segmented into individual cardiac cycles by the segmenter 105. The Discrete Fourier Transform (DFT) of each individual cardiac cycle may be generated and stored in a memory (not shown). The template selector 107 selects the cycle with the largest SNR as the template.

It is to be noted that for the purpose of this disclosure, the ratio of the energy content of the cycle below a predetermined frequency including the predetermined frequency and the energy content of the cycle above the predetermined frequency is treated as the SNR. Even though the heart sounds are predominantly in the range of 0-200 Hz some heart sounds, like clicks and murmurs lie in the higher frequency ranges. However, for the purposes of this description 200 Hz, for example, may be designated as the threshold frequency. One may also choose any other predetermined frequency as the threshold, since, unlike in the case of filtering, the signals on either side of the threshold are not lost. It is also possible that the threshold frequency is also user selectable.

Once the template is selected, the difference generator 109 subtracts its DFT from the DFT of each of the remaining cycles. The subtraction yields a DFT of a component of each cycle—called the extracted component hereafter. Thus, the signal of each cycle is the sum of the DFT of the template and the DFT of the extracted component.

The inverse Fourier transform generator 111A generates the inverse Fourier transforms the DFT of the template and the inverse Fourier transform generator 111B generates the inverse Fourier transform of the DFT of the extracted component. The inverse Fourier transform of the DFT of the template is repeatedly replayed in synchronism, cycle by cycle, with the concatenated inverse Fourier transform of the DFT of the extracted component of each cycle. These signals are amplified through amplifiers 113A and 113B respectively. The two amplifiers have separate, independent user controllable amplification controls. These allow a user to set the amplification or attenuation of each of the components during replay.

The combiner 115 outputs the combined output 117 for use by a user. The combined signal may be power amplified by a power amplifier (not shown) to drive a pair of headphones or such for a user to listen to the sounds. The user may then vary the amplification of each of the components above to suit his needs. Alternatively, the replayed signals may be conveyed to an assisted diagnosis device that analyses the signals and determines pathologies of the heart, if any.

It is to be understood that the independent amplifiers 113A and 113B and combiner 115 are shown as different blocks in the schematic diagram and the description, all of them may be incorporated in a single block such as a summing amplifier with independently variable impedances connected to the input or where the amplitude of the input signals are varied by variable voltage dividers and are summed by a summing amplifier with constant gain. All such variations are to be treated as variations of the device described above.

To eliminate the high frequency noises which are not related to the heart sounds in any manner whatsoever from this signal, a low-shelf filter (a shelving filter) may also be used. This is for only cutting off the signals in the frequencies beyond which there are no signals useful in auscultation or assisted diagnosis but purely of random nature unrelated to the heart sounds. These may include screeching noises from furniture or hinges of doors or beeps of patient monitoring devices.

The description hitherto has been oriented towards an offline or non real time device wherein the heart sounds are first recorded or stored and then processed as described above. However the heart sounds may be processed in real time also, which will be described briefly below.

In a device which is operating on the heart sounds recorded or stored before hand, the SNR of each of the cycles is first calculated and then it is used to operate on the remaining cycles. In the case of the real time device, when a cycle that has a SNR greater than a predetermined threshold is encountered, it is designated as the template and the process of subtraction is carried out on the subsequent cycles acquired in real time. However, the SNR of each of the cycles that is acquired is also calculated. Whenever a cycle is encountered which has an SNR greater than the present template, the present template is discarded and the new cycle is used as a template. This may have the advantage that auscultation may be started right away when the diagnostician places the sensor on the thorax of a subject without having to wait for the predetermined number of cycles to be recorded. Further, as time progresses, the signal quality of the output is likely to improve as newer cycles with higher SNR are encountered. It may also have the advantage that the memory required to store the predetermined number of cycles of the heart sound is not needed.

In an embodiment 200 of the disclosed device the electrocardiogram (ecg) electrodes, collectively shown as 219, sense the ecg signals of the subject and are also acquired simultaneously with the heart sounds by ecg receiver 204. The ecg signals are used to segment the heart sound into individual cycles. Although the cycles can be segmented without the aid of the ecg signals, it is easier to do so with the ecg signals. This may have the advantage of requiring lesser processing time for the segmentation and may be advantageous when the signals are being processed in real time.

In either of the embodiments it possible to process the signals either in real time or on previously stored signals and store the results in a memory for later playback—to another expert for a second opinion, to an automated diagnosis assistance device or as a teaching aid to playback the sounds to teach auscultation, for example.

An additional feature is that the device allows a user to listen only to sounds like breathing sounds, clicks and murmurs by suppressing the sounds of the rhythmic heart beats altogether.

It is to be understood that only the novel features of the device are described so as to keep the description clear and concise. A skilled person will be aware of and will be in a position to fill in the other details necessary to build the disclosed device. However, the other details are described below for the sake of completeness.

The sensor for the heart sounds could be of any type viz. any type of microphone, a piezoelectric sensor and so on. The segmenter 105 may use any method to segment the heart sound signals to individual cycles. It may be advantageous to use the additionally sensed ecg signal to segment the sounds as the ecg signals are the signals that precede and give rise to the heart sound signals. It is known that the length of the cardiac cycles vary from cycle to cycle. Thus the selected template and the individual heart cycles have different cycle lengths. This necessitates re-sampling the template or the signal of each cycle to enable the difference generator to subtract. Further before replaying the concatenated extracted signal and the repeatedly played template, the extracted signal has to be restored to the original cycle duration and the time duration of the template has to be matched to that of the extracted signal by re-sampling appropriately. These steps and device blocks needed to achieve them have not been described in detail as these are known techniques that a skilled person would be aware of how to implement, once provided with the other details of the disclosed invention.

Further, a method 300 of processing heart signals is disclosed herein. The method comprises the following steps after the heart sounds are acquired, in a known way, for instance by using a microphone or piezoelectric transducer and such. In one variant of the method, the acquired signals are stored in digital form in a memory after sampling or as a high fidelity analog recording.

In a segmentation step 321, single cycles of the heart sound signal are segmented. Then in the Fourier transform step 323, the DFT of each segment is obtained and stored. In a signal to noise ratio determination step 325 the DFTs are analyzed to determine the SNR of each of the cycles. Since the sounds in the frequency range of 0-200 Hz have maximum heart sound energy, for the purposes of this disclosure the sounds in that range are considered to be "signal" and the rest are considered "noise". A different threshold may however be chosen and the invention is independent of the chosen threshold. Thus the SNR is the ratio of the energy of the spectrum of frequencies below 200 Hz and the energy above 200 Hz. In a selection step the cycle with the largest SNR is selected as the template. It has to be clarified here that the term SNR is used to signify the components of the signal above and below a threshold but the noise is not eliminated. The heart sound signal, the "lub-dub" sound, is predominantly in the frequency range of 0-200 Hz and other heart and other related and unrelated sounds may be in the range above 200 Hz. These other sounds could be the clicks, thrills and murmurs of the heart that are also heart sounds and sounds such as breathing sounds, and external noises such as screeching noises from furniture and creaking noises from door hinges and beeps of monitoring equipment normally found in hospitals.

In an extraction step 327, the DFT of the template is subtracted from the DFT of each the cycles. This separates the heart sounds into two parts, viz. the template and an extracted component that has frequency components not matching the template and therefore higher noise. It is to be noted that if the DFT of the template and the DFT of the extracted component of any cycle are added, the original cycle results. Thus each cycle is the sum of the DFT of the template and the extracted signal.

In a restoration step 329 the inverse Fourier transform of each of the extracted component and the template are obtained. Thus, from the Fourier transform step 323 to the restoration step 329 the method is carried out in the frequency domain. Further, in the restoration step 329 the Inverse Fourier Transform of the extracted signal are concatenated and the template is concatenated with itself repeatedly. This results in the original heart sound signal when the two are replayed in synchronism. In an amplification step 331, the two concatenated signals are amplified with user controllable or user selectable amplification factors. The two amplified signals are added together in a summation step 333 for being output to a user or listener for diagnosis.

In an advantageous variant 400 of the method, the segmentation of the individual heart cycles are assisted by ecg signals processed in a ecg signal processing step 435. In this variant, the cycle of the heart beat sound signal is segmented depending on the ecg signal as the reference.

It is to be noted that the details of certain steps are excluded from the description to bring out the salient features of the disclosed method. However the steps that are required to be carried out to implement the disclosed method are described briefly hereunder.

In the segmentation step 321 any known method to segmenting the heart sound signals into individual cycles may be used. It may be advantageous to use the ecg signals to segment the sounds as the ecg signals are the signals that precede and give rise to the heartbeat and hence the heart sounds. It is known that the length of the cardiac cycles vary from cycle to cycle. Thus the selected template and the individual heart cycles have different cycle lengths. This may necessitate re-sampling the template or the signal of each cycle to carry out the extraction step 327. Further, in the restoration step, the inverse Fourier transform of the extracted signal and the template signal, the extracted signal has to be restored to the original cycle duration and the time duration of the template has to be have the same cycle duration as that of the extracted signal by re-sampling appropriately. These steps needed to achieve them have not been described in detail as these are known techniques that a skilled person would be aware of how to implement, once provided with the other details of the disclosed invention.

Other variations to the disclosed embodiments can be thought of by those skilled in the art, in practicing the claimed invention, from a study of the drawings, the disclosure, and the appended claims. All such variations are to deemed to be variants of the disclosed device and method. In the claims, the word "comprising" does not exclude elements or steps other than those mentioned, and the indefinite article "a" or "an" does not exclude a plurality. A single circuit block or other unit may fulfill the functions of several items recited in the claims. The mere fact that certain measures are recited in mutually different dependent claims does not indicate that a combination of these measures cannot be used to advantage.

The invention claimed is:

1. A heart monitoring device comprising:
a sensor configured to sense acoustic heart sounds and output cardiac signals;
a processing device configured to:
  segment the acoustic cardiac signals into individual heart sound cycle signals;
  Fourier transform each of the individual heart sound cycle signals;
  select one of the Fourier transformed individual heart sound cycle signals with a large signal to noise ratio as a template signal;
  subtract the template signal from each of the other Fourier transformed individual heart sound cycle signals to obtain an extracted component signal for each individual heart sound cycle signal;
  inverse Fourier transform the template signal and each of the extracted component signals;
amplifiers configured to independently amplify the inverse Fourier transformed extracted component signals and the inverse Fourier transformed template signals;
a signal combiner configured to combine the amplified inverse Fourier signal transformed template signal and each of the amplified inverse Fourier transformed extracted component signals to generate a combined signal; and
at least one of:
a device configured to convert the combined signal into acoustic sound to facilitate determining heart pathologies and
a machine assisted diagnosis device configured to determine heart pathologies based on the combined signal.

2. The device of claim 1, further including:
an electrocardiogram signal receiver configured to receive an electrocardiogram signal and wherein the processing device is further configured to segment the individual heart sound cycle of the cardiac signal based on the sensed electrocardiogram signal.

3. The device of claim 1, further including:
a memory configured to store the sensed cardiac signals and wherein the processing device is further configured to select an individual heart sound cycle signal having a largest signal to noise ratio among the individual heart sound cycles greater than a predetermined threshold, from all the individual heart sound cycles stored in the memory as the template signal.

4. The device of claim 1, wherein the processing device is configured to receive the cardiac signals continuously and select a first individual heart sound cycle signal with a signal to noise ratio above a predetermined threshold signal to noise ratio as a new template signal and replace the present template signal with the new present template signal in response to a subsequent individual heart sound cycle signal having a greater signal to noise ratio than the present template signal.

5. The device of claim 4, wherein the acoustic playback device includes headphones.

6. The device of claim 1, wherein the at least one of the device configured to convert the combined signal into sounds and an assisted diagnosis device configured to determine heart pathologies is a pair of headphones.

7. A method of cardiac monitoring, the method comprising the steps of:
 receiving an acoustic heart beat signal from an acoustic heart beat sensor;
 with a processor, segmenting single cycles of the acoustic heart beat signal;
 with the processor, carrying out a Fourier transform of the segmented single cycles;
 with the processor, determining signal to noise ratios of the Fourier transformed single cycles;
 with the processor, selecting a one of the Fourier transformed single cycles with a largest signal to noise ratio as a template;
 with the processor, subtracting the template from each of the other Fourier transformed single cycles to obtain extracted components;
 with the processor, inverse Fourier transforming each of the extracted components and inverse Fourier transforming the template;
 with an amplifier, controllably independently amplifying each of the inverse Fourier transformed extracted components and the inverse Fourier transformed template;
 adding the amplified inverse Fourier transformed template and of each of the inverse Fourier transformed extracted components to form a combined signal; and
 at least one of converting the combined signal into acoustic sound for playback to a clinician with an acoustic playback device and implementing an assisted diagnosis of the combined signal using the processor.

8. The method of claim 7 wherein the single heart beat cycle is determined based on an electrocardiogram signal.

9. The method of claim 7, wherein determining the signal to noise ratio includes for each single cycle, determining a ratio of energy of the single cycle below a predetermined frequency to an energy of the single cycle above the predetermined frequency.

10. The method of claim 7, wherein the heart beat signals are received from a memory or acquired continuously from a subject in real time.

11. The method of claim 7, wherein the heart beat signals are retrieved from a memory, and the inverse Fourier transformed extracted components are concatenated before amplification and are outputted in a continuous loop.

12. A heart monitoring device comprising:
 an acoustic sensor configured to sense acoustic cardiac signals;
 a segmenter configured to segment the acoustic cardiac signal into segmented individual heart sound cycles;
 a Fourier transform device configured to Fourier transform each of the individual heart sound cycles;
 a selector configured to select one of the Fourier transformed individual heart sound cycles with a largest signal to noise ratio as a template;
 a difference generator configured to subtractively combine the template and other Fourier transformed individual heart sound cycles to obtain an extracted component for each of the individual heart sound cycles;
 an inverse Fourier transformer configured to inverse Fourier transform the template and each of the extracted components;
 independent amplifiers configured to independently and controllably amplify the inverse Fourier transformed extracted components and independently amplify the inverse Fourier transformed template;
 a signal combiner configured to combine the amplified inverse Fourier transformed templates and each of the amplified inverse Fourier transformed extracted components to generate a combined output signal; and
 an acoustic device configured to convert the combined signal into acoustic sound.

* * * * *